United States Patent [19]

Hanover

[11] Patent Number: 5,583,909
[45] Date of Patent: Dec. 10, 1996

[54] C-ARM MOUNTING STRUCTURE FOR MOBILE X-RAY IMAGING SYSTEM

[75] Inventor: Barry K. Hanover, Salt Lake City, Utah

[73] Assignee: OEC Medical Systems, Inc., Salt Lake City, Utah

[21] Appl. No.: 360,211

[22] Filed: Dec. 20, 1994

[51] Int. Cl.$^6$ ............................................. H05G 1/02
[52] U.S. Cl. .......................... 378/197; 378/193; 378/198
[58] Field of Search ................................ 378/193, 196, 378/197, 198, 187, 189

[56] References Cited

U.S. PATENT DOCUMENTS

| | | | |
|---|---|---|---|
| 4,955,046 | 9/1990 | Siczek et al. | 378/197 |
| 5,014,293 | 5/1991 | Boyd et al. | 378/197 |
| 5,226,069 | 7/1993 | Narita | 378/189 |

*Primary Examiner*—Don Wong
*Attorney, Agent, or Firm*—Thorpe North & Western, L.L.P.

[57] ABSTRACT

A C-arm apparatus. A C-shaped member is slidably supported in a suspended position by a support arm. The support arm is rotatable about an axis of lateral rotation and is slidably mounted to an outer circumference of the arc-shaped member at a point of attachment coinciding with the axis of lateral rotation. Since the support arm is attached to the C-shaped member in alignment with the axis of lateral rotation, the support arm does not introduce eccentric lateral moment-arm action during lateral rotation and thereby provides a more stabile, balanced support structure.

22 Claims, 2 Drawing Sheets

C-ARM MOUNTING STRUCTURE FOR MOBILE X-RAY IMAGING SYSTEM

BACKGROUND OF THE INVENTION

1. The Field of the Invention

The present invention relates generally to C-arm support structure and a method for mounting the same, and more particularly to a support arm which is slidably mounted to the back of a C-arm at a point of attachment which forms a horizontal line with a center of curvature of the C-arm.

2. The Background Art

It is often desirable to take X-rays of a patient from a number of different positions, preferably without the need for frequent repositioning of the patient. It is preferable that the X-ray support structure not unduly encumber the space immediately surrounding the patient to enable a physician to treat or otherwise attend to the patient without the need to repeatedly remove and replace the X-ray equipment. Mobile C-arm X-ray diagnostic equipment has been developed to meet these needs and has become well known in the medical art of surgical and other interventional procedures.

A C-arm refers generally to an elongate C-shaped member terminating in opposing distal ends of the "C" shape. An X-ray source and an image receptor are typically mounted at or near the distal ends, respectively, of the C-arm in opposing orientation, with the C-arm supported in a suspended position. The space within the C-shape of the arm provides room for the physician to attend to the patient substantially free of interference from the X-ray support structure. The support structure usually rests upon wheels which enable the C-arm to be wheeled from room to room, and along the length of a patient while the physician operates or examines, ensuring that devices such as cardiac catheters, long bone nails, etc. are properly positioned during the procedure.

The C-arm is usually mounted so as to enable rotational movement of the arm in two degrees of freedom, i.e. about two perpendicular axes in a spherical motion. More specifically, the C-arm is slidably mounted to the support structure to enable orbiting rotational movement of the C-arm about its center of curvature, thereby permitting the X-ray source and the image receptor to be selectively oriented vertically, horizontally, or somewhere in between. The C-arm is also laterally rotatable, i.e. in a perpendicular direction relative to the orbiting direction to enable selectively adjustable positioning of the X-ray source and receptor relative to both the width and length of the patient. The spherically rotational aspects of C-arm apparatus allow the physician to take X-rays of the patient at an optimal angle as determined with respect to the particular anatomical condition being imaged.

Designers and manufacturers of C-arm equipment are faced with a number of challenges. The support structure used to support and rotate a C-arm in its various suspended positions must be strong enough to withstand tremendous torsional, tensile and compressive stresses. The support structure must also be heavy enough and have a large enough footprint to avoid tipping over upon lateral rotation of the C-arm, which causes the center of gravity to shift dramatically. There have been previous attempts to provide C-arm support structure to solve the problems mentioned above. Exemplary of such prior art attempts is U.S. Pat. No. 4,955,046 (issued to Siczek et al. on Sep. 4, 1990) which discloses a C-arm apparatus. A wheeled support cart includes a rotatable L-arm upon which a C-arm is slidably mounted. The L-arm thus provides rotational movement of the C-arm in two degrees of freedom.

The prior art C-arm apparatuses such as that disclosed in the U.S. Pat. No. '046 Siczek et al. patent, while useful, are characterized by a number of disadvantages. The mounting structure of the image receptor often encumbers the adjacent sides and/or back convex portion of the C-arm, thereby preventing the main support structure from slidably attaching to that portion of the C-arm. This condition prevents complete horizontal positioning of the image receptor, and necessitates the use of the prior art L-arm. The L-arm attaches to the C-arm at some point below a horizontal extension of the center of curvature of the C-arm, thus permitting the C-arm to slide the image receptor to a horizontal position relative to the center of curvature.

Although the L-arm permits the desired horizontal positioning, it introduces other problems. When the L-arm is rotated, increased lateral moment-arm action is introduced to the system which reduces the system's capacity to avoid tipping. Put another way, the range of motion is reduced and the instability introduced by the L-arm requires a smaller C-arm for given dimensions of the support apparatus. The L-arm itself introduces extra eccentric weight to the system which aggravates the tipping problem. The L-arm design requires sophisticated counter-balancing devices such as is taught in the U.S. Pat. No. '046 Siczek et al. patent. Unpowered C-arm systems have utilized an axis of rotation through the center of mass of the C-arm/L-arm assembly but not through the axis of rotation of the C-arm. High-voltage cables necessary to power the X-ray equipment must be longer in order to traverse the added length of the L-arm, thereby increasing exposed portions of the cables.

OBJECTS AND SUMMARY OF THE INVENTION

It is therefore an object of the present invention to provide a C-arm apparatus for use with X-ray diagnostic equipment and the like.

It is another object of the invention to provide such a C-arm apparatus which is less susceptible to tipping caused by lateral rotation of the C-arm.

It is an additional object of the invention to provide such a C-arm apparatus which utilizes a lighter support arm.

It is still another object of the invention to provide such a C-arm apparatus which is capable of utilizing a shorter high-voltage power supply cable.

It is a further object of the invention to provide such a C-arm apparatus which requires less external exposure of the power supply cable.

It is an additional object of the invention to provide such a C-arm apparatus capable of manipulating a much larger C-arm without increasing the overall dimensions of the support apparatus.

It is another object of the invention to provide such a C-arm apparatus capable of a greater range of orbital and lateral motion.

It is yet another object of the invention to provide such a C-arm apparatus which is simple in design and operation.

It is a further object of the invention, in accordance with one aspect thereof, to provide such a C-arm apparatus with increased capacity to maintain balance.

The above objects and others not specifically recited are realized in a specific illustrative embodiment of a C-arm apparatus. A C-shaped member is slidably supported in a suspended position by a support arm. The support arm is rotatable about an axis of lateral rotation and is slidably mounted to an outer circumference of the arc-shaped member at a point of attachment coinciding with the axis of lateral rotation. Since the support arm is attached to the C-shaped member in alignment with the axis of lateral rotation, the support arm does not introduce eccentric lateral moment-arm action during lateral rotation and thereby provides a more stabile, balanced support structure and eliminates the need for motor drive requirements.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION

Figure 1:
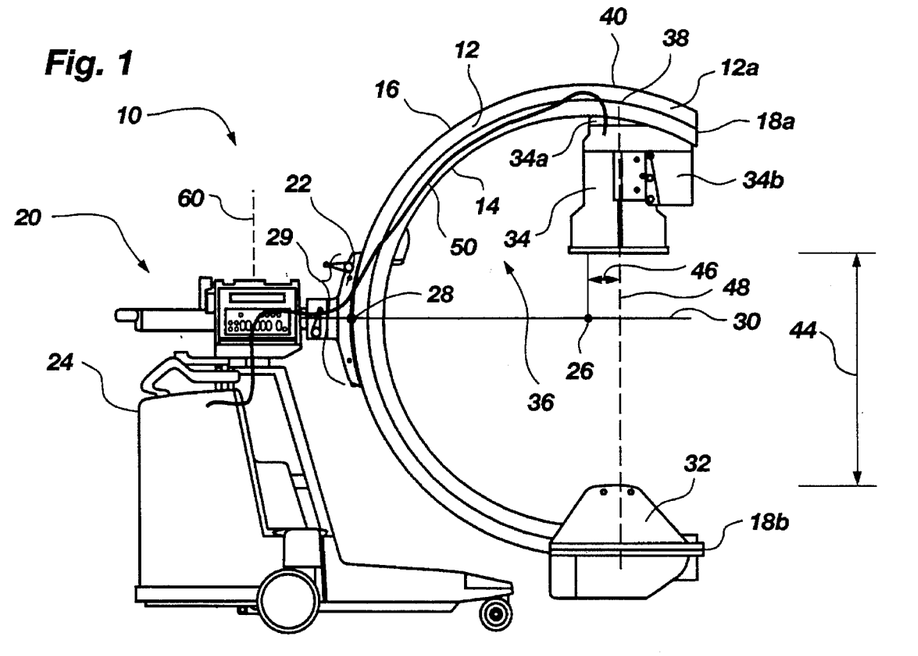
FIG. 1 is a side view of a C-arm apparatus made in accordance with the principles of the present invention.

A preferred embodiment in accordance with the present invention is illustrated in FIG. 1 wherein is shown a C-arm X-ray apparatus, generally designated at 10. The apparatus 10 includes a C-arm 12 having inner and outer circumferences 14 and 16, respectively, and terminating in opposing upper and lower distal ends 18a and 18b. The C-arm 12 preferably has a uniformly circular C-shape, but may alternatively comprise any arc-shaped member.

The C-arm 12 is held in a suspended position by support means such as structure, generally designated at 20, which includes a support arm 22 mounted upon a wheeled base 24. The support arm 22 provides for rotational movement of the C-arm 12 about an axis of lateral rotation 30, either by a bearing assembly between the support arm 22 and the C-arm 12, or by the support 22 itself being rotatably mounted with respect to the base 24.

The wheeled base 24 enables transport of the C-arm 12 from a first location to a second location. As such, the wheels of the base operate as transporting means coupled to the support structure 20 for transporting the support arm 22 and the C-arm 12 from a first location to a second location. It is often highly advantageous to be able to move X-ray equipment from one room to another conveniently. The mobile nature of the apparatus 10 as provided by the wheeled base 24 offers the advantage of increased access by patients in many different rooms of a hospital, for example.

The support arm 22 is slidably mounted to the outer circumference 16 of the C-arm 12 and the support structure 20 includes structure and mechanisms necessary to enable selective, sliding orbital motion of the C-arm about an axis of orbital rotation 26 to a selected position. The axis 26 preferably coincides with a center of curvature of the C-arm 12 and with the axis of lateral rotation 30. It will be appreciated that the sliding orbital motion causes the C-arm 12 to move through various sliding points of attachment 28 to the support arm 22. The support structure 20 further includes mechanisms known in the art for laterally rotating the support arm 22 selectable amounts about an axis of lateral rotation 30 to a selected lateral position. The combination of sliding orbital motion and lateral rotation enables manipulation of the C-arm in two degrees of freedom, i.e. about two perpendicular axes. This provides a kind of spherical quality to the movability of the C-arm 12—the sliding orbital motion and lateral rotation enable an X-ray source 32 coupled to the C-arm to be moved to substantially any latitude/longitude point on a lower hemisphere of an imaginary sphere about which the C-arm is moveable.

The apparatus 10 includes an X-ray source 32 and an image receptor 34 as known generally in the X-ray diagnostic art, mounted upon opposing locations, respectively, on the C-arm 12. The X-ray source 32 and the image receptor 34 may be referred to collectively as the X-ray source/image receptor 32/34. The image receptor 34 can be an image intensifier or the like. The orbital and laterally rotational manipulation of the C-arm enables selective positioning of the X-ray source/image receptor 32/34 with respect to the width and length of a patient located within interior free space 36 of the C-arm 12. The sliding orbital movement of the C-arm causes the X-ray source/image receptor 32/34 to move along respective arcuate movement paths. The image receptor 34 is preferably secured to the inner circumference 14 of the C-arm 12 and the X-ray source 32 may also be secured to said inner circumference 14, the significance of which will be described below.

Key aspects of the present invention include the mounted positions of the image receptor 34 and the C-arm 12. These mounted positions result in the axis of lateral rotation 30 substantially coinciding with the point of attachment 28 of the C-arm 12 to the support arm 22 for substantially any position of the C-arm 12. The significance of this feature includes that rotation of the support arm 22 does not introduce eccentric lateral moment-arm action so as to provide a more stabile, balanced support structure. A related aspect of a preferred embodiment is that the center of mass of the C-arm 12 coincides with the axis 30 for any position of the C-arm.

Figure 2:
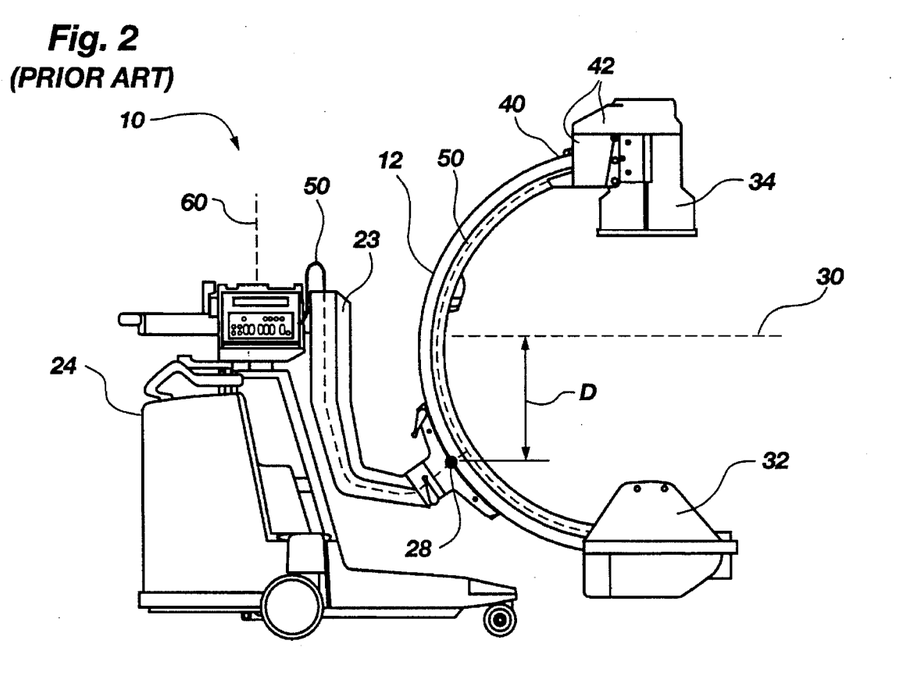
FIG. 2 is a side view of a C-arm apparatus exemplary of known prior art C-arm devices.

It will be appreciated that prior art C-arm support structure, exemplified in FIG. 2, includes a downwardly-extending L-arm 23 such that its point of attachment 28 with the C-arm 12 resides a distance D away from the axis of lateral rotation 30. The image receptor 34 on the prior art C-arms are mounted and positioned in such a way as to encumber a back convex portion 40 of the C-arm 12, as shown by encumbering portions 42 in FIG. 2, thereby preventing the support arm 23 from slidably attaching to that portion 12a of the C-arm. In order to achieve complete horizontal positioning of the image receptor 34, the L-arm was developed to attach to the C-arm the point of attachment 28 below the axis of lateral rotation 30, thus permitting the C-arm 12 to slide the image receptor 34 to at least a horizontal orientation. This introduces an eccentric lateral moment arm D upon lateral rotation of the C-arm 12 about the axis 30, bringing the entire apparatus 10 out of balance and thereby reducing the degree of lateral rotation achievable about the axes 30 and 60 without creating the potential for tipping the apparatus 10 over. This typically requires lateral rotation of the C-arm 12 about the axis 30 to be electrically powered to overcome the torque which results from the imbalance.

Figure 3:
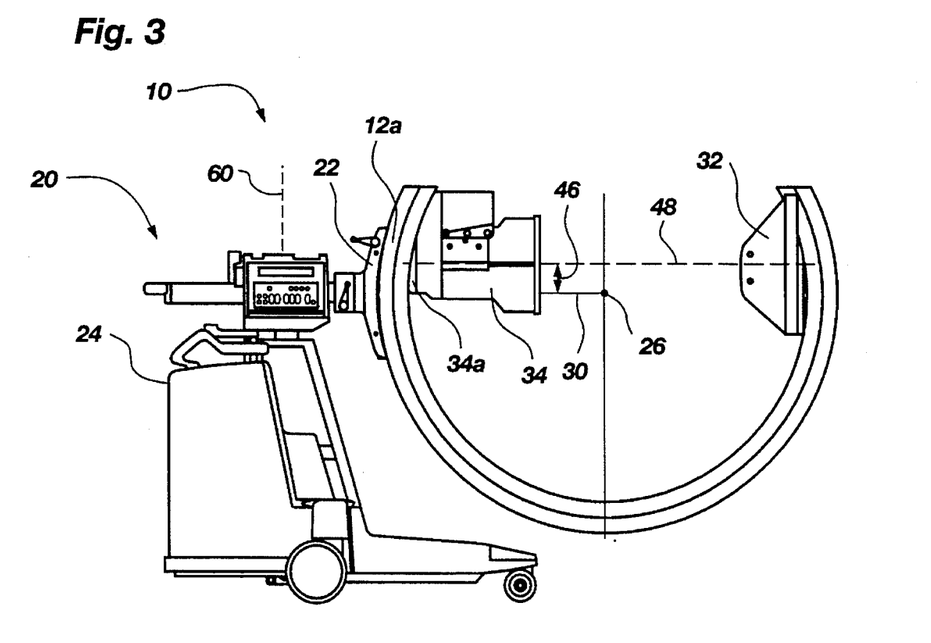
FIG. 3 is a side view of the C-arm apparatus of FIG. 1 showing the C-arm in a first rotated position.

Applicant has discovered the inventive combination of the image receptor 34 positioned such that the support arm 22 resides outside the arcuate movement path of the image receptor 34, to prevent interfering contact between the receptor and the support arm 22. This can be achieved by a support arm which attaches only to the rear surface of the C-arm and coupling the image receptor 34 only to the inside-surface of the C-arm (as shown in FIG. 1), or by otherwise locating the image receptor 34 so as not to encumber slidable movement tracks engagable by the support arm 22. For example, the support arm 22 can be slidably mounted to the C-arm 12 without circumscribing the C-arm as shown in FIGS. 1 and 3, in a manner sufficient to avoid interfering contact between the support arm and the image receptor 34 when the C-arm is slid a sufficient distance relative to the support arm to bring a rear portion 34a of the image receptor to a location adjacent to the sliding point of attachment to the support arm 22, as shown specifically in FIG. 3. This enables slidable movement of the C-arm 12 to a point of attachment with the support arm 12 immediately adjacent to a rear portion 34a of the image receptor 34, as shown in FIG. 3. The encumbering portions 42 (FIG. 2) of the prior art configuration prevent the support arm 22 from attaching to the C-arm 12 immediately adjacent to the rear portion 34a of the image receptor 34, a problem which is solved by the present invention as shown in FIG. 3.

The support arm 22 of applicant's invention is thus able to reside completely outside of the arcuate movement path of the image receptor 34 so as to enable slidable attachment of the support arm 22 to substantially any portion of the C-arm 12. This eliminates the need for an L-arm and permits applicant's support arm 22 to be laterally rotatable about an axis of lateral rotation 30 which coincides with the point of the attachment 28, thereby eliminating the eccentric, lateral moment arm D caused by the L-arm 23 (FIG. 2) of the prior art C-arm devices.

Figure 4:
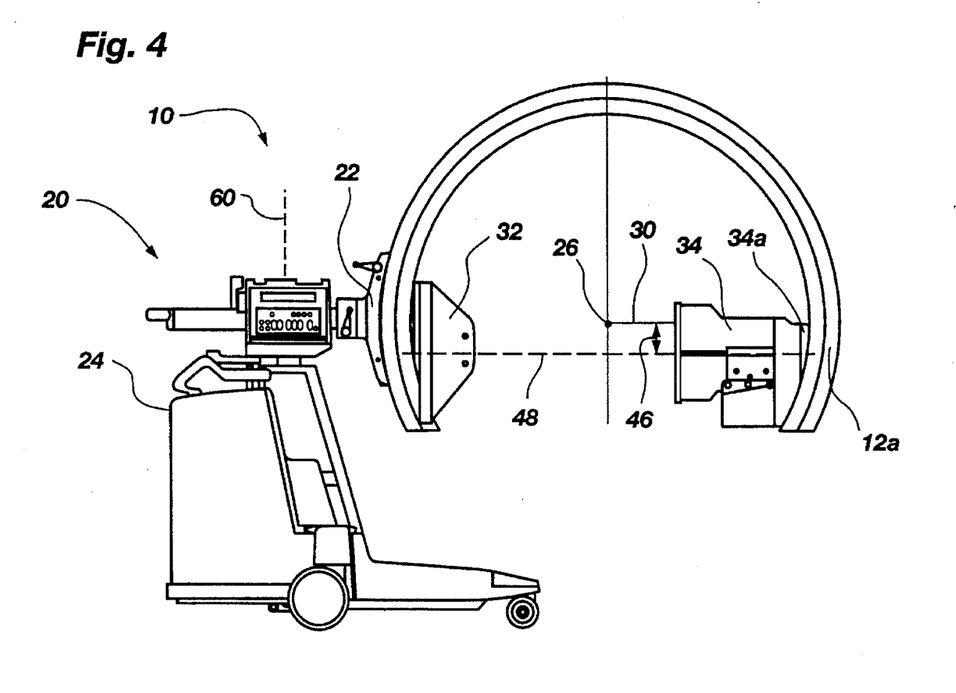
FIG. 4 is a side view of the C-arm apparatus of FIG. 3 showing the C-arm in a second rotated position.

The X-ray source 32 can also be designed and positioned, when desired, such that the support arm 22 resides outside of an arcuate movement path of said X-ray source 32, in the same manner as described above with respect to the image receptor 34. This enables slidable movement of the C-arm 12 to a point of attachment with the support arm 12 immediately adjacent to a rear portion of the X-ray source 32 as shown in FIG. 4, with advantages similar to those described with respect to positioning of the image receptor 34. Accordingly, while the X-ray source 32 of FIG. 1 has an encumbering housing 45 which blocks movement of said X-ray source 32 to a point adjacent the support arm 12, FIGS. 3 and 4 show an alternative embodiment whereby the X-ray source 32 resides inside the C-arm 12 so as to enable the X-ray source 32 to slide to a position adjacent the support arm 22 as in FIG. 4.

The removal of the image receptor 34 arcuate movement path outside the boundaries of the support arm 22, and the elimination of the L-arm 23, provides a number of advantages. The range of orbital motion of the C-arm about the axis 26 is substantially increased to +101° and −63° in applicant's preferred embodiment as shown in FIG. 1. The elimination of the lateral moment arm D eliminates the need for a complex electrically-powered motor drive or other counter-balancing structure as taught in the prior art discussed above in the section entitled "The Background Art." For a given desired distance 44 between the X-ray source/ image receptor 32/34, a larger C-shape can be used for the C-arm 12 without substantially increasing the overall machine height, thereby increasing the interior free space 36 available for a physician to work in. A high voltage cable assembly 50 required to supply adequate power to the X-ray source/image receptor 32/34 must allow for multiple combinations of movement of the C-arm 12 and support arm 22, and the exposed portion of the cable assembly 50 can thus be much shorter by elimination of the L-arm 23, as inspection of FIGS. 1 and 2 will illustrate. The elimination of the eccentric lateral moment arm D provides an increased range of lateral rotation of the C-arm about the axis 30 for a given weight of the support structure 20, through minimization of the potential for tipping. The apparatus 10 may also be provided with rotational capacity for rotational movement about an axis 60, which movement is also increased in range by elimination of the eccentric lateral moment arm D.

An additional inventive aspect of the present invention includes the location of a power supply 34b of the image receptor 34. By locating the power supply 34b toward the C-arm opening as shown in FIG. 1, the image receptor 34 and the X-ray source 32 can be moved closer to the center of curvature 26, thereby reducing the distance 46 and thus improving overall balance of the apparatus 10. It is necessary for balancing purposes to have a distance 46 between a line of alignment 48 and the intersection of the axes 26 and 30. The line of alignment 48 refers to alignment of a central beam produced by the X-ray source 32, and the image receptor 34. It is desirable, for purposes of maintaining the anatomy being imaged within the imaging plane while the C-arm 12 is being repositioned, that this distance 46 be as short as possible. Locating the power supply 34b toward the C-arm opening (i.e. closer to the distal end 18a of the C-arm 12 as shown in FIG. 1) instead of inside the X-ray source/ receptor line of alignment 48 allows the distance 46 to be minimized.

Securing the image receptor 34 to the inner circumference 14 of the C-arm 12 is a preferred way to cause the support arm 22 to reside outside of the arcuate movement path of the image receptor. However, it will be appreciated that there are numerous alternative structural combinations which provide for placement of the support arm 22 outside of this arcuate movement path, all of which are within the scope of the present invention. For example, the support arm 22 can be designed so as to permit interfering structure 42 such as that shown in FIG. 2 to pass within the structure of the support arm during sliding orbital motion of the C-arm 12.

It is preferred that the axis of lateral rotation 30 pass through the center of curvature 26 of the C-arm 12 in a substantially horizontal orientation, although such is not required. As noted above, the C-arm 12 may embody any suitable arc-shaped member, although a uniformly circular C-arm having a single center of curvature is preferred. However, an arc-shaped member having multiple centers of curvature may be used with the present invention, in which case it is preferred that the axis of lateral rotation 30 coincide with the center of curvature of the portion of the arc-shaped member to which the support arm 22 is attached for a given position of the arc-shaped member.

Although applicant has referred to the attachment of the support arm 22 to the C-arm 12 as a "point of attachment 28", it will be appreciated that in practice, the support arm is essentially attached to the C-arm over an area 29 and not a point, although a "point" may be a large area or a small site. The phrase "point of attachment" as used herein shall refer generally to some central point 28 within the area of attachment 29. The central point of attachment 28 preferably coincides with a geometric centroid of the area of attachment 29. It is also to be understood that the phrase "slidably mounted" as used herein shall include any suitable mounting of the C-arm 12 to the support arm 22 which enables an orbital, circulating-type motion of the C-arm about the axis 26. The phrase "slidably mounted" is thus not to be limited to literal sliding action but may include stepped advancement achieved with notched structure, geared advancement, or any other suitable advancement means.

A presently preferred method for manufacturing a C-arm apparatus with a support arm aligned to an axis of lateral rotation includes the steps of:

(a) forming an arc-shaped member having opposing inner and outer circumferences;

(b) forming support means for supporting the arc-shaped member in a suspended position, said support means including (i) a support arm, (ii) sliding means for sliding an object to which the support arm is slidably mounted a selectable amount through various points of attachment to the support arm, and (iii) rotating means for laterally rotating the support arm a selectable amount about an axis of lateral rotation to a selected lateral position;

(c) slidably mounting the support arm to the outer circumference of the arc-shaped member at a point of attachment to thereby enable the sliding means to cause sliding orbital motion of said arc-shaped member about an axis of orbital rotation to a selected position, such that the axis of lateral rotation substantially coincides with the point of attachment of the arc-shaped member to the support arm for any position of the arc-shaped member.

A presently preferred method for manufacturing a C-arm apparatus with a support arm residing outside of an arcuate movement path of an image receptor includes the steps of:

(a) forming an arc-shaped member having opposing inner and outer circumferences;

(b) forming support means for supporting the arc-shaped member in a suspended position, said support means including a support arm and sliding means for sliding by a selectable amount an object to which the support arm is slidably mounted;

(c) slidably mounting a support arm to the outer circumference of the arc-shaped member to thereby enable the sliding means to cause sliding orbital motion of said arc-shaped member about an axis of orbital rotation to a selected position; and (d) mounting an X-ray source and an image receptor upon opposing locations, respectively, on the arc-shaped member such that the sliding means causes the X-ray source and the image receptor to move along respective arcuate movement paths, further including the step of positioning the image receptor such that the support arm resides outside the arcuate movement path of said image receptor to thereby prevent interfering contact between the image receptor and the support arm and to enable slidable movement of the arc-shaped member to a point of attachment with the support arm immediately adjacent to a rear portion of said image receptor.

Those skilled in the art will appreciate that the scope of the present invention encompasses many combinations and a broad spectrum of features and structures equivalent to those specifically discussed herein. The principles of the invention may thus be used in any setting requiring the advantages thereof. Those having ordinary skill in the field of this invention will appreciate the advantages of the invention and its application to a wide variety of uses.

The present invention represents a significant advance in the field of X-ray positioning devices. It is noted that many, but not all, of the advantages of the present invention accrue due to the combination of the support arm 22 residing outside of an arcuate movement path of the image receptor 34, and the use of the support arm 22 instead of the prior art L-arm 23. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A mobile C-arm apparatus for use with X-ray diagnostic equipment, said apparatus comprising:

an arc-shaped member having opposing inner and outer circumferences;

an image receptor mounted upon the inner circumference of the arc-shaped member and having a rear portion;

support means attached to the arc-shaped member for supporting said arc-shaped member in a suspended position, said support means including (i) a support arm which is slidably mounted to the outer circumference of the arc-shaped member at a sliding point of attachment thereto without circumscribing and extending into the inner circumference the arc-shaped member, in a manner sufficient to avoid interfering contact between the support arm and the image receptor when said arc-shaped member is slid a sufficient distance relative to said support arm to bring the rear portion of the image receptor to a location adjacent to the sliding point of attachment to the support arm, (ii) sliding means for sliding said arc-shaped member relative to the support arm a selectable amount through various points of attachment to the support arm to thereby enable sliding orbital motion of said arc-shaped member about an axis of orbital rotation to a selected position, and (iii) rotating means for laterally rotating the support arm a selectable amount about an axis of lateral rotation to a selected lateral position; and a wheeled transporting means coupled to the support means for wheeling the support means and the arc-shaped member from a first location to a second location, wherein said transporting means is configured and dimensioned to enable manual movement and guidance of the apparatus from one room to another in a health care facility;

wherein the axis of lateral rotation substantially coincides with the point of attachment of the arc-shaped member to the support arm for any position of said arc-shaped member.

2. Apparatus as defined in claim 1, further comprising:

an X-ray source, wherein said X-ray source and the image receptor are mounted upon opposing locations, respectively, on the arc-shaped member such that the sliding means causes the X-ray source and the image receptor to move along respective arcuate movement paths, the image receptor being positioned such that the support arm resides outside the arcuate movement path of said image receptor to thereby prevent interfering contact between the image receptor and the support arm and to enable slidable movement of the arc-shaped member to a point of attachment with the support arm immediately adjacent to a rear portion of said image receptor.

3. Apparatus as defined in claim 1, further comprising:

an X-ray source, wherein said X-ray source and the image receptor are mounted upon opposing locations, respectively, on the arc-shaped member such that the sliding means causes the X-ray source and the image receptor to move along respective arcuate movement paths, the X-ray source being positioned such that the support arm resides outside the arcuate movement path of said X-ray source to thereby prevent interfering contact between the X-ray source and the support arm and to enable slidable movement of the arc-shaped member to a point of attachment with the support arm immediately adjacent to a rear portion of said X-ray source.

4. Apparatus as defined in claim 2, wherein the arc-shaped member includes opposing distal ends and wherein the apparatus further includes a power supply to the image receptor which resides closer to one of said distal ends than does said image receptor to thereby enable a line of alignment of a central beam produced by the X-ray source and the image receptor to reside closer to the center of the arc-shaped member.

5. Apparatus as defined in claim 2, wherein the support arm is mounted only to the outer circumference of the arc-shaped member, and wherein the image receptor is coupled only to the inner circumference of the arc-shaped member.

6. Apparatus as defined in claim 1, further comprising an X-ray source and an image receptor mounted upon opposing locations, respectively, on the arc-shaped member, such that the rotating means for laterally rotating the support arm causes corresponding lateral rotational movement of the X-ray source and receptor to thereby enable selective lateral positioning of said X-ray source and image receptor.

7. A C-arm apparatus as defined in claim 1, wherein the support arm is horizontally aligned relative to a center of curvature of the arc-shaped member such that a horizontal line passing through said center of curvature substantially coincides with the point of attachment of the arc-shaped member to the support arm for any position of said arc-shaped member.

8. A mobile C-arm apparatus for use with X-ray diagnostic equipment, said apparatus comprising:

an arc-shaped member having opposing inner and outer circumferences;

mobile support means attached to the arc-shaped member for supporting said arc-shaped member in a suspended position and for transporting said arc-shaped member from a first location to a second location, said support means including (i) a support arm slidably mounted to the outer circumference of the arc-shaped member so as not to circumscribe said arc-shaped member and contact or engage the inner circumference of said arc-shaped member, and (ii) sliding means for sliding said arc-shaped member relative to the support arm a selectable amount through various points of attachment to the support arm to thereby enable sliding orbital motion of said arc-shaped member about an axis of orbital rotation to a selected position; and an X-ray source and an image receptor mounted upon opposing locations, respectively, on the arc-shaped member such that the sliding means causes the X-ray source and the image receptor to move along respective arcuate movement paths, the image receptor being positioned such that the support arm resides outside the arcuate movement path of said image receptor to thereby prevent interfering contact between the image receptor and the support arm and to enable slidable movement of the arc-shaped member to a point of attachment with the support arm immediately adjacent to a rear portion of said image receptor.

9. Apparatus as defined in claim 8, wherein the X-ray source is positioned such that the support arm resides outside the arcuate movement path of said X-ray source to thereby prevent interfering contact between the X-ray source and the support arm and to enable slidable movement of the arc-shaped member to a point of attachment with the support arm immediately adjacent to a rear portion of said X-ray source.

10. Apparatus as defined in claim 8, wherein the arc-shaped member includes opposing distal ends and wherein the apparatus further includes a power supply to the image receptor which resides closer to one of said distal ends than does said image receptor to thereby enable a line of alignment of a central beam produced by the X-ray source and image receptor to reside closer to the center of the arc-shaped member.

11. Apparatus as defined in claim 8, wherein the image receptor is disposed upon the inner circumference of the arc-shaped member.

12. Apparatus as defined in claim 10, wherein the support arm is horizontally aligned relative to a center of curvature of the arc-shaped member such that a horizontal line passing through said center of curvature substantially coincides with the point of attachment of the arc-shaped member to the support arm for any position of said arc-shaped member.

13. Apparatus as defined in claim 12, wherein the support means further includes rotating means for laterally rotating the support arm a selectable amount about the horizontal line to cause corresponding rotational movement of the arc-shaped member about said horizontal line to thereby selectively laterally position the X-ray source and image receptor.

14. A method for manufacturing a C-arm apparatus for use with X-ray diagnostic equipment, said method comprising the steps of:

(a) forming an arc-shaped member having opposing inner and outer circumferences, and mounting an image receptor having a rear portion upon the inner circumference of the arc-shaped member;

(b) forming support means for supporting the arc-shaped member in a suspended position, said support means including (i) a support arm, and (ii) rotating means for laterally rotating the support arm a selectable amount about an axis of lateral rotation to a selected lateral position;

(c) slidably mounting the support arm to the outer circumference of the arc-shaped member at a point of attachment without circumscribing and extending into the inner circumference the arc-shaped member, in a manner sufficient to avoid interfering contact between the support arm and the image receptor when said arc-shaped member is slid a sufficient distance relative to said support arm to bring the rear portion of the image receptor to a location adjacent to the sliding point of attachment to the support arm, such that said arc-shaped member is slidable in orbital motion relative to said support arm about an axis of orbital rotation to a selected position, such that the axis of lateral rotation substantially coincides with the point of attachment of the arc-shaped member to the support arm for any position of the arc-shaped member; and (d) coupling a wheeled transporting means to the support means for wheeling the support means and the arc-shaped member from a first location to a second location, wherein said transporting means is configured and dimensioned to enable manual movement and guidance of the apparatus from one room to another in a health care facility.

15. A method as defined in claim 14, further comprising the step of:

(d) mounting an X-ray source and an image receptor upon opposing locations, respectively, on the arc-shaped member such that the sliding means causes the X-ray source and the image receptor to move along respective arcuate movement paths, further including the step of positioning the image receptor such that the support arm resides outside the arcuate movement path of said image receptor to thereby prevent interfering contact between the image receptor and the support arm and to enable slidable movement of the arc-shaped member to a point of attachment with the support arm immediately adjacent to a rear portion of said image receptor.

16. A method as defined in claim 15, further comprising the step of:

(e) securing the image receptor to the inner circumference of said arc-shaped member.

17. A method as defined in claim 14, further comprising the step of:

(f) mounting an X-ray source and an image receptor upon opposing locations, respectively, on the arc-shaped member such that the rotating means causes corresponding lateral rotational movement of the X-ray source and image receptor to thereby enable selective lateral positioning of said X-ray source and image receptor.

18. A method as defined in claim 14, wherein step (c) further comprises horizontally aligning the support arm relative to a center of curvature of the arc-shaped member such that a horizontal line passing through said center of curvature substantially coincides with the point of attachment of the arc-shaped member to the support arm for any position of said arc-shaped member.

19. A method for manufacturing a C-arm apparatus for use with X-ray diagnostic equipment, said method comprising the steps of:

(a) forming an arc-shaped member having opposing inner and outer circumferences;

(b) forming support means for supporting the arc-shaped member in a suspended position and for transporting said arc-shaped member from a first location to a second location, said support means including a support arm and sliding means for sliding by a selectable amount an object to which the support arm is slidably mounted;

(c) slidably mounting a support arm to the outer circumference of the arc-shaped member such that said support arm avoids circumscribing and extending into the inner circumference of said arc-shaped member, and such that said support arm also avoids contacting or engaging with the inner circumference of said arc-shaped member, to thereby enable the sliding means to cause sliding orbital motion of said arc-shaped member about an axis of orbital rotation to a selected position; and (d) mounting an X-ray source and an image receptor upon opposing locations, respectively, on the arc-shaped member such that the sliding means causes the X-ray source and the image receptor to move along respective arcuate movement paths, further including the step of positioning the image receptor such that the support arm resides outside the arcuate movement path of said image receptor to thereby prevent interfering contact between the image receptor and the support arm and to enable slidable movement of the arc-shaped member to a point of attachment with the support arm immediately adjacent to a rear portion of said image receptor.

20. A method as defined in claim 19, further comprising the step of:

(e) securing the image receptor to the inner circumference of said arc-shaped member.

21. A method as defined in claim 19, wherein step (c) further comprises mounting the support arm to the outer circumference of the arc-shaped member at a point of attachment which coincides with a horizontal line passing through a center of curvature of said arc-shaped member at said point of attachment.

22. A method as defined in claim 21, wherein step (b) further comprises forming the support means to include rotating means for laterally rotating the support arm a selectable amount about the horizontal line to cause corresponding rotational movement of the arc-shaped member about said horizontal line to thereby selectively laterally position the X-ray source and image receptor.

* * * * *

(12) REEXAMINATION CERTIFICATE (4299th)
United States Patent
Hanover (10) Number: US 5,583,909 C1
(45) Certificate Issued: Mar. 27, 2001

(54) C-ARM MOUNTING STRUCTURE FOR MOBILE X-RAY IMAGING SYSTEM

(75) Inventor: Barry K. Hanover, Salt Lake City, UT (US)

(73) Assignee: OEC Medical Systems, Inc., Salt Lake City, UT (US)

Reexamination Request:
No. 90/005,226, Jan. 21, 1999

Reexamination Certificate for:
Patent No.: 5,583,909
Issued: Dec. 10, 1996
Appl. No.: 08/360,211
Filed: Dec. 20, 1994

(51) Int. Cl.$^7$ .................................................. H05G 1/02
(52) U.S. Cl. .......................... 378/197; 378/193; 378/198
(58) Field of Search .................................. 378/187, 189, 378/193, 196, 197, 198

(56) References Cited

U.S. PATENT DOCUMENTS

| | | |
|---|---|---|
| Re. 34,943 | 5/1995 | Van Endschot et al. . |
| 3,281,598 | 10/1966 | Hollstein . |
| 4,209,706 | 6/1980 | Nunan . |
| 4,298,801 | 11/1981 | Heitman et al. . |
| 4,447,721 | 5/1984 | Wang . |
| 4,653,083 | 3/1987 | Rossi . |
| 4,716,581 | 12/1987 | Barud . |
| 4,768,216 | 8/1988 | Harvey et al. . |
| 4,775,994 | 10/1988 | Kranvogel . |
| 4,797,907 | 1/1989 | Anderton . |
| 4,802,197 | 1/1989 | Juergens . |
| 4,887,287 | 12/1989 | Cobben . |
| 4,955,046 | 9/1990 | Siczek et al. . |
| 4,961,214 | 10/1990 | Van Endschot et al. . |
| 4,964,151 | 10/1990 | Trotel . |
| 5,014,293 | 5/1991 | Boyd et al. . |
| 5,038,371 | 8/1991 | Janssen et al. . |
| 5,050,204 | 9/1991 | Siczek et al. . |
| 5,067,145 | 11/1991 | Siczek et al. . |
| 5,226,069 | 7/1993 | Narita . |
| 5,283,808 | 2/1994 | Cramer et al. . |
| 5,305,368 | 4/1994 | Bisek et al. . |
| 5,339,350 | 8/1994 | Thelosen . |
| 5,426,683 | 6/1995 | O'Farrell, Jr. et al. . |
| 5,436,461 | 7/1995 | Saffer et al. . |
| 5,475,730 | 12/1995 | Galando . |
| 5,506,882 | 4/1996 | O'Farrell, Jr. et al. . |
| 5,521,957 | 5/1996 | Hansen . |
| 5,544,217 | 8/1996 | Kadowaki et al. . |
| 5,586,162 | 12/1996 | Grichnik . |

FOREIGN PATENT DOCUMENTS

| | | |
|---|---|---|
| 3138916 A1 | 4/1983 | (DE) . |
| 85 21 246 | 3/1986 | (DE) . |
| 89 06 386 | 5/1989 | (DE) . |
| 41 37 724 A1 | 5/1992 | (DE) . |
| 40 37 054 C1 | 6/1992 | (DE) . |
| 0 023 051 | 1/1981 | (EP) . |
| 0 160 749 | 11/1985 | (EP) . |
| 0 350 996 | 7/1989 | (EP) . |
| 0 430 338 | 6/1991 | (EP) . |
| 0 488 991 A1 | 6/1992 | (EP) . |
| 1459093 | 2/1967 | (FR) . |
| 2671507 | 7/1992 | (FR) . |
| 2 098 440 | 11/1982 | (GB) . |
| WO 95/25419 | 9/1995 | (WO) . |

OTHER PUBLICATIONS

International ISS Surgical Systems, Inc. ISS–2000 Plus Multispecialty Surgical Imaging System Brochure, pp. 1–25, 1991, Phoenix, Arizona.

*Primary Examiner*—David P. Porta (57) ABSTRACT

A C-arm apparatus. A C-shaped member is slidably supported in a suspended position by a support arm. The support arm is rotatable about an axis of lateral rotation and is slidably mounted to an outer circumference of the arc-shaped member at a point of attachment coinciding with the axis of lateral rotation. Since the support arm is attached to the C-shaped member in alignment with the axis of lateral rotation, the support arm does not introduce eccentric lateral moment-arm action during lateral rotation and thereby provides a more stabile, balanced support structure.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–22 is confirmed.

New claims 23–26 are added and determined to be patentable.

23. *A mobile C-arm apparatus for use with X-ray diagnostic equipment, said apparatus comprising:*
   *an arc-shaped member having opposing inner and outer circumferences;*
   *an image receptor mounted upon the inner circumference of the arc-shaped member and having a rear portion;*
   *support means attached to the arc-shaped member for supporting said arc-shaped member in a suspended position, said support means including (i) a support arm which is slidably mounted to the outer circumference of the arc-shaped member at a sliding point of attachment thereto without circumscribing and extending into the inner circumference the arc-shaped member, in a manner sufficient to avoid interfering contact between the support arm and the image receptor when said arc-shaped member is slid a sufficient distance relative to said support arm to bring the rear portion of the image receptor to a location adjacent to the sliding point of attachment to the support arm, (ii) sliding means for sliding said arc-shaped member relative to the support arm a selectable amount through various points of attachment to the support arm to thereby enable sliding orbital motion of said arc-shaped member about an axis of orbital rotation to a selected position, and (iii) rotating means for laterally rotating the support arm a selectable amount about an axis of lateral rotation to a selected lateral position; and*
   *a wheeled transporting means coupled to the support means for wheeling the support means and the arc-shaped member from a first location to a second location, wherein said transporting means is configured and dimensioned to enable manual movement and guidance of the apparatus from one room to another in a health care facility;*
   *wherein the axis of lateral rotation substantially coincides in horizontal alignment with the point of attachment of the arc-shaped member to the support arm for any position of said arc-shaped member.*

24. *A mobile C-arm apparatus for use with X-ray diagnostic equipment, said apparatus comprising:*
   *an arc-shaped member having opposing inner and outer circumferences;*
   *mobile support means attached to the arc-shaped member for supporting said arc-shaped member in a suspended position and for transporting said arc-shaped member from a first location to a second location, said support means including (i) a support arm slidably mounted to the outer circumference of the arc-shaped member so as not to circumscribe said arc-shaped member and contact or engage the inner circumference of said arc-shaped member, and (ii) sliding means for sliding said arc-shaped member relative to the support arm a selectable amount through various points of attachment to the support arm to thereby enable sliding orbital motion of said arc-shaped member about an axis of orbital rotation to a selected position; and*
   *an X-ray source and an image receptor mounted upon opposing locations, respectively, on the arc-shaped member such that the sliding means causes the X-ray source and the image receptor to move along respective arcuate movement paths, the image receptor being positioned such that the support arm resides outside the arcuate movement path of said image receptor to thereby prevent interfering contact between the image receptor and the support arm and wherein the support arm being slidably mounted is configured and arranged to be engagable along substantially the enter length of the arc-shaped member between the X-ray source and the image receptor to enable slidable movement of the arc-shaped member to a point of attachment with the support arm immediately adjacent to a rear portion of said image receptor.*

25. *A method for manufacturing a C-arm apparatus for use with X-ray diagnostic equipment, said method comprising the steps of:*
   *(a) forming an arc-shaped member having opposing inner and outher circumferences, and mounting an image receptor having a rear portion upon the inner circumference of the arc-shaped member;*
   *(b) forming support means for supporting the arc-shaped member in a suspended position, said support means including (i) a support arm, and (ii) rotating means for laterally rotating the support arm a selectable amount about an axis of lateral rotation to a selected lateral position;*
   *(c) slidably mounting the support arm to the outer circumference of the arc-shaped member at a point of attachment without circumscribing and extending into the inner circumference the arc-shaped member, in a manner suficient to avoid interfering contact between the support arm and the image receptor when said arc-shaped member is slid a sufficient distance relative to said support arm to bring the rear portion of the image receptor to a location adjacent to the sliding point of attachment to the support arm, such that said arc-shaped member is slidable in orbital motion relative to said support arm about an axis of orbital rotation to a selected position and wherein the support arm being slidably mounted is configured and arranged to be engagable along substantially the enter length of the arc-shaped member between the X-ray source and the image receptor, such that the axis of lateral rotation substantially coincides in horizontal alignment with the point of attachment of the arc-shaped member to the support arm for any position of the arc-shaped member; and*
   *(d) coupling a wheeled transporting means to the support means for wheeling the support means and the arc-shaped member from a first location to a second location, wherein said transporting means is configured and dimensioned to enable manual movement and guidance of the apparatus from one room to another in a health care facility.*

26. A method for manufacturing a C-arm apparatus for use with X-ray diagnostic equipment, said method comprising the steps of:

(a) forming an arc-shaped member having opposing inner and outer circumferences;

(b) forming support means for supporting the arc-shaped member in a suspended position and for transporting said arc-shaped member from a first location to a second location, said support means including a support arm and sliding means for sliding by a selectable amount an object to which the support arm is slidably mounted;

(c) slidably mounting a support arm to the outer circumference of the arc-shaped member such that said support arm avoids circumscribing and extending into the inner circumference of said arc-shaped member, and such that said support arm also avoids contacting or engaging with the inner circumference of said arc-shaped member, to thereby enable the sliding means to cause sliding orbital motion of said arc-shaped member about an axis of orbital rotation to a selected position; and (d) mounting an X-ray source and an image receptor upon opposing locations, respectively, on the arc-shaped member such that the sliding means causes the X-ray source and the image receptor to move along respective arcuate movement paths, further including the step of positioning the image receptor such that the support arm resides outside the arcuate movement path of said image receptor to thereby prevent interfering contact between the image receptor and the support arm and wherein the support arm being slidably mounted is configured and arranged to be engagable along substantially the enter length of the arc-shaped member between the X-ray source and the image receptor and to enable slidable movement of the arc-shaped member to a point of attachment with the support arm immediately adjacent to a rear portion of said image receptor.

* * * * *